US008105596B2

(12) United States Patent
Goldenberg

(10) Patent No.: US 8,105,596 B2
(45) Date of Patent: *Jan. 31, 2012

(54) IMMUNOTHERAPY OF B-CELL MALIGNANCIES USING ANTI-CD22 ANTIBODIES

(75) Inventor: David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/048,223

(22) Filed: Mar. 15, 2011

(65) Prior Publication Data

US 2011/0165073 A1 Jul. 7, 2011

Related U.S. Application Data

(60) Division of application No. 09/965,796, filed on Oct. 1, 2001, now Pat. No. 7,910,103, which is a continuation of application No. 09/307,816, filed on May 10, 1999, now Pat. No. 6,306,393, which is a continuation-in-part of application No. 09/038,955, filed on Mar. 12, 1998, now Pat. No. 6,183,744.

(60) Provisional application No. 60/041,506, filed on Mar. 24, 1997.

(51) Int. Cl.
| | |
|---|---|
| A61K 35/14 | (2006.01) |
| A61K 39/00 | (2006.01) |
| A61K 39/395 | (2006.01) |
| C07K 1/00 | (2006.01) |
| C07K 14/00 | (2006.01) |
| C07K 16/00 | (2006.01) |
| C12P 21/08 | (2006.01) |

(52) U.S. Cl. ............ 424/141.1; 424/130.1; 424/133.1; 424/134.1; 424/135.1; 424/136.1; 424/138.1; 424/144.1; 424/152.1; 424/154.1; 424/155.1; 424/156.1; 424/174.1; 424/178.1; 424/181.1; 424/183.1; 530/350; 530/386; 530/387.1

(58) Field of Classification Search .................. None
See application file for complete search history.

(56) References Cited

U.S. PATENT DOCUMENTS

| | | | |
|---|---|---|---|
| 5,106,955 | A | 4/1992 | Endo et al. |
| 5,484,892 | A | 1/1996 | Tedder et al. |
| 5,686,072 | A | 11/1997 | Uhr et al. |
| 5,698,178 | A | 12/1997 | Goldenberg |
| 5,789,554 | A | 8/1998 | Leung et al. |
| 6,183,744 | B1 | 2/2001 | Goldenberg |
| 6,306,393 | B1 | 10/2001 | Goldenberg |
| 7,837,995 | B2 * | 11/2010 | Goldenberg ............ 424/141.1 |

FOREIGN PATENT DOCUMENTS

| | | |
|---|---|---|
| EP | 510 949 A2 | 10/1992 |
| WO | 95/09917 A1 | 4/1995 |
| WO | 96/04925 A1 | 2/1996 |
| WO | 98/42378 A1 | 10/1998 |
| WO | 99/02567 A2 | 1/1999 |

OTHER PUBLICATIONS

Webster's II New Riverside University Dictionary, p. 307, Houghton Mifflin Company, Boston, MA, 1984.
Li et al.; "The Epitope Specificity and Tissue Reactivity of Four Murine Monoclonal Anti-CD22 Antibodies"; Cellular Immunology 118: 85-99, 1989.
Rudikoff et al.; "Single amino acid substitution altering antigen-binding specificity"; Proc. Natl. Acad. Sci. USA 79; 1979-1983, Mar. 1982.
Kiesel et al.; "Removal of Cells from a malignant B-cell line from bone marrow with immunomagnetic beads and with complement . . . "; Leukemia Research vol. II, No. 12, 1987, pp. 1119-1125.
Press; "Prospects for the Management of Non-Hodgkin's Lymphomas with Monoclonal Antibodies and Immunoconjugates"; The Cancer Journal from Scientific American, vol. 4, supplement 2, pp. S19-S26, 1998.
Maloney et al.; "Phase 1 clinical trial using escalating single-dose infusion of chimeric anti-CD20 monoclonal Antibody (IDEC-C2B8) in patients with recurrent B-cell lymphoma"; Blood, vol. 84, No. 8, 1994, pp. 2457-2466.
Ghetie et al.; "Evaluation of Ricin A Chain-containing Immunotoxins Directed against CD19 and CD22 Antigens on Normal and Malignant Human B-Cells as Potential Reagents for in Vivo Therapy"; Cancer Research, 1988, 48, 2610-2617.
Flavell et al.; "Systematic Therapy with 3BIT, a triple combination cocktail of anti-CD19, -CD22, and -CD38-Saporin Immunotoxin, is curative of human B-Cell . . . "; Cancer Research, vol. 57, No. 21, Nov. 1997, pp. 4824-4829.
Green et al.; "Antigen-specific human monoclonal antibodies from mice engineered with hum lg heavy and light Chain YACS"; Nature Genetic, vol. 1, May 1994, pp. 13-21.
French et al.; "Response of B-cell lymphomato a combination of bispecific antibodies and saporin"; Leukemia Research, vol. 20, No. 7, Jul. 1996, pp. 607-617.

(Continued)

Primary Examiner — Alana H Dent
(74) Attorney, Agent, or Firm — Rossi, Kimms & McDowell LLP

(57) ABSTRACT

B-cell malignancies, such as the B-cell subtype of non-Hodgkin's lymphoma and chronic lymphocytic leukemia, are significant contributors to cancer mortality. The response of B-cell malignancies to various forms of treatment is mixed. Traditional methods of treating B-cell malignancies, including chemotherapy and radiotherapy, have limited utility due to toxic side effects. Immunotherapy with anti-CD20 antibodies have also provided limited success. The use of antibodies that bind with the CD22 or CD19 antigen, however, provides an effective means to treat B-cell malignancies such as indolent and aggressive forms of B-cell lymphomas, and acute and chronic forms of lymphatic leukemias. Moreover, immunotherapy with anti-CD22 and/or anti-CD19 antibodies requires comparatively low doses of antibody protein, and can be used effectively in multimodal therapies.

21 Claims, No Drawings

OTHER PUBLICATIONS

Renner et al.; "Monoclonal antibodies in the treatment of non-Hodgkin's Lymphoma: recent results and Future Prospects"; Leukemia, vol. 11, No. suppl.2, Apr. 1997, pp. 555-559.

Leonard et al.; "Epratuzumab, A New Anti-CD22, Humanized, Monoclonal Antibody for the Therapy of Non-Hodgkin's Lymphoma (NHL): Phase I/II Trial Results"; Blood, vol. 94, No. 10 suppl. 1 part 1, 1999, Abstract $404.

Kaminski et al.; "Radioimmunotherapy of B-Cell lymphoma with [131] Anti-B1 [Anti-CD20' Antibody"; New England J. of Medicine, Aug. 12, 1993, 329(7): 459-465.

Vuist et al.; "Potentiation by Interleukin 2 of Burkitt's Lymphoma Therapy with Anti-Pan B (Anti-CD19) Monoclonal Antibodies in a Mouse Xenotransplantation Model"; Cancer Research, Jul. 15, 1989, 49, 3783-3788.

Juweid et al.; "Treatment of non-hodgkin's lymphoma with radiolabeled murine, chimeric, or humanized LL2, an anti-CD22"; Cancer Research (Suppl.) vol. 55, Dec. 1, 1995, pp. 5899s-5907s.

Kreitman et al.; "Psendomonas Exotoxin-based Immunotoxins Containing the Antibody LL2 or LL2-tab Induce Regression of Subcutaneous Human B-cell Lymphomas in Mice"; Cancer Research 53:819-825, Feb. 15, 1993.

* cited by examiner

IMMUNOTHERAPY OF B-CELL MALIGNANCIES USING ANTI-CD22 ANTIBODIES

This application is a divisional of U.S. patent application Ser. No. 09/965,796 filed Oct. 1, 2001; which is a continuation of U.S. patent application Ser. No. 09/307,816 filed May 10, 1999 (now U.S. Pat. No. 6,306,393); which is a continuation-in-part of U.S. patent application Ser. No. 09/038,955 filed Mar. 12, 1998 (now U.S. Pat. No. 6,183,744); which claims priority to U.S. Provisional Application No. 60/041,506 filed Mar. 24, 1997, the contents of each of which are incorporated herein by reference in their entirety.

BACKGROUND OF THE INVENTION

1. Field of the Invention

The present invention relates to immunotherapeutic methods for treating B-cell malignancies. In particular, this invention is directed to methods for treating B-cell malignancies by administering comparatively low doses of antibody that binds to the CD22 antigen or antibody that binds to the CD19 antigen. The present invention also is directed to multimodal therapeutic methods in which anti-CD22 or anti-CD19 administration is supplemented with chemotherapy, or by administration of therapeutic proteins, such as immunoconjugates and antibody fusion proteins.

2. Background

B-Cell lymphomas, such as the B-cell subtype of non-Hodgkin's lymphoma, are significant contributors to cancer mortality. The response of B-cell malignancies to various forms of treatment is mixed. For example, in cases in which adequate clinical staging of non-Hodgkin's lymphoma is possible, field radiation therapy can provide satisfactory treatment. Still, about one-half of the patients die from the disease. Devesa et al., *J. Nat'l Cancer Inst.* 79:701 (1987).

The majority of chronic lymphocytic leukemias are of B-cell lineage. Freedman, *Hematol. Oncol. Clin. North Am.* 4:405 (1990). This type of B-cell malignancy is the most common leukemia in the Western world. Goodman et al., *Leukemia and Lymphoma* 22:1 (1996). The natural history of chronic lymphocytic leukemia falls into several phases. In the early phase, chronic lymphocytic leukemia is an indolent disease, characterized by the accumulation of small mature functionally-incompetent malignant B-cells having a lengthened life span.

Eventually, the doubling time of the malignant B-cells decreases and patients become increasingly symptomatic. While treatment can provide symptomatic relief, the overall survival of the patients is only minimally affected. The late stages of chronic lymphocytic leukemia are characterized by significant anemia and/or thrombocytopenia. At this point, the median survival is less than two years. Foon et al., *Annals Int. Medicine* 113:525 (1990). Due to the very low rate of cellular proliferation, chronic lymphocytic leukemia is resistant to treatment.

Traditional methods of treating B-cell malignancies, including chemotherapy and radiotherapy, have limited utility due to toxic side effects. The use of monoclonal antibodies to direct radionuclides, toxins, or other therapeutic agents offers the possibility that such agents can be delivered selectively to tumor sites, thus limiting toxicity to normal tissues.

Antibodies against the CD20 antigen have been investigated for the therapy of B-cell lymphomas. For example, a chimeric anti-CD20 antibody, designated as "IDEC-C2B8," has activity against B-cell lymphomas when provided as unconjugated antibodies at repeated injections of doses exceeding 500 mg per injection. Maloney et al., *Blood* 84:2457 (1994); Longo, *Curr. Opin. Oncol.* 8:353 (1996). About 50 percent of non-Hodgkin's patients, having the low-grade indolent form, treated with this regimen showed responses. Therapeutic responses have also been obtained using $^{131}$I-labeled B1 anti-CD-20 murine monoclonal antibody when provided as repeated doses exceeding 600 mg per injection. Kaminski et al., *N. Engl. J. Med.* 329:459 (1993); Press et al., *N. Engl. J. Med.* 329:1219 (1993); Press et al., *Lancet* 346:336 (1995). However, these antibodies, whether provided as unconjugated forms or radiolabeled forms, have not shown objective responses in patients with the more prevalent and lethal form of B-cell lymphoma, the intermediate or aggressive type.

A need exists to develop an immunotherapy for B-cell malignancies that allows repeated administration of comparatively low doses of an antibody, and that is not limited by the necessity of adding a toxic agent for achieving a therapeutic response of significant duration

SUMMARY OF THE INVENTION

Accordingly, it is an object of the present invention to provide a method for treating B-cell malignancies using comparatively low doses of anti-CD22 and/or anti-CD19 antibodies.

It is a further object of this invention to provide multimodal methods for treatment of B-cell malignancies in which low doses of anti-CD22 and/or anti-CD19 antibodies are supplemented with the administration of a therapeutic protein, such as an immunoconjugate or antibody fusion protein, or by a chemotherapeutic regimen.

These and other objects are achieved, in accordance with one embodiment of the present invention, by the provision of a method of treating a B-cell malignancy, comprising the step of administering to a subject having a B-cell malignancy an anti-CD22 antibody and a pharmaceutically acceptable carrier.

DETAILED DESCRIPTION

1. Overview

As discussed above, anti-CD20 antibodies, whether unconjugated or labeled with a therapeutic radionuclide, have failed to provide objective responses in patients with intermediate or aggressive forms of B-cell lymphoma. Surprisingly, clinical studies with patients having non-Hodgkin's lymphoma (both indolent and aggressive forms) or acute lymphatic leukemia have demonstrated that relatively low dosess (i.e., 20-100 mg protein per dose) of unconjugated murine or humanized anti-CD22 antibody, designated as either "EPB-2" or "LL2," can induce partial or complete remissions lasting up to 24 months. This, despite the fact that such patients are often in relapse after multiple courses of aggressive chemotherapy, and even after bone marrow grafting. The positive results with unconjugated anti-CD22 antibody are particularly surprising in advanced patients with the aggressive (intermediate) form of non-Hodgkin's lymphoma and in chronic and acute lymphatic leukemia, since unconjugated or radiolabeled anti-CD20 antibodies have failed to show such effects, particularly at low protein doses. Moreover, the positive results with anti-CD22 antibodies are unexpected in view of the statement by Freedman, *Hematol. Oncol. Clin. North Am.* 4:405 (1990), that chronic lymphocytic leukemias of the B-cell type do not generally express CD22.

2. Definitions

In the description that follows, and in the documents incorporated by reference herein, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

An isolated DNA molecule is a fragment of DNA that is not integrated in the genomic DNA of an organism. For example, a cloned antibody gene is a DNA fragment that has been separated from the genomic DNA of a mammalian cell. Another example of an isolated DNA molecule is a chemically-synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

An antibody fragment is a portion of an antibody such as F(ab')$_2$, F(ab)$_2$, Fab', Fab, and the like. Regardless of structure, an antibody fragment binds with the same antigen that is recognized by the intact antibody. For example, an anti-CD22 monoclonal antibody fragment binds with an epitope of CD22.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

A chimeric antibody is a recombinant protein that contains the variable domains and complementary determining regions derived from a rodent antibody, while the remainder of the antibody molecule is derived from a human antibody.

Humanized antibodies are recombinant proteins in which murine complementarity determining regions of a monoclonal antibody have been transferred from heavy and light variable chains of the murine immunoglobulin into a human variable domain.

As used herein, a therapeutic agent is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A naked antibody is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term antibody component includes both an entire antibody and an antibody fragment.

An immunoconjugate is a conjugate of an antibody component with a therapeutic agent.

As used herein, the term antibody fusion protein refers to a recombinant molecule that comprises one or more antibody components and a therapeutic agent. Examples of therapeutic agents suitable for such fusion proteins include immunomodulators ("antibody-immunomodulator fusion protein") and toxins ("antibody-toxin fusion protein"). The fusion protein may comprise a single antibody component, a multivalent combination of different antibody components or multiple copies of the same antibody component.

3. Production of Anti-CD22 and Anti-CD19 Monoclonal Antibodies, Humanized Antibodies, Primate Antibodies and Human Antibodies Rodent monoclonal antibodies to CD22 or CD19 can be obtained by methods known to those skilled in the art. See generally, for example, Kohler and Milstein, Nature 256:495 (1975), and Coligan et al. (eds.), CURRENT PROTOCOLS IN IMMUNOLOGY, VOL. 1, pages 2.5.1-2.6.7 (John Wiley & Sons 1991) ["Coligan"]. Briefly, monoclonal antibodies can be obtained by injecting mice with a composition comprising CD22 or CD19, verifying the presence of antibody production by removing a serum sample, removing the spleen to obtain B-lymphocytes, fusing the B-lymphocytes with myeloma cells to produce hybridomas, cloning the hybridomas, selecting positive clones which produce anti-CD22 or anti-CD19 antibodies, culturing the clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Suitable amounts of the well-characterized CD22 or CD19 antigen for production of antibodies can be obtained using standard techniques. As an example, CD22 can be immunoprecipitated from B-lymphocyte protein using the deposited antibodies described by Tedder et al., U.S. Pat. No. 5,484,892 (1996).

Alternatively, CD22 protein or CD19 protein can be obtained from transfected cultured cells that overproduce CD22 or CD19. Expression vectors that comprise DNA molecules encoding CD22 or CD19 proteins can be constructed using published CD22 and CD19 nucleotide sequences. See, for example, Wilson et al., *J. Exp. Med.* 173:137 (1991); Wilson et al., *J. Immunol.* 150:5013 (1993). As an illustration, DNA molecules encoding CD22 or CD19 can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., *Gene* 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize genes as large as 1.8 kilobases in length. Adang et al., *Plant Molec. Biol.* 21:1131 (1993); Bambot et al., *PCR Methods and Applications* 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993).

In a variation of this approach, anti-CD22 or anti-CD19 monoclonal antibody can be obtained by fusing myeloma cells with spleen cells from mice immunized with a murine pre-B cell line stably transfected with CD22 cDNA or CD19 cDNA. See Tedder et al., U.S. Pat. No. 5,484,892 (1996).

One example of a suitable murine anti-CD22 monoclonal antibody is the LL2 (formerly EPB-2) monoclonal antibody, which was produced against human Raji cells derived from a Burkitt lymphoma. Pawlak-Byczkowska et al., *Cancer Res.* 49:4568 (1989). This monoclonal antibody has an $IgG_{2a}$ isotype, and the antibody is rapidly internalised into lymphoma cells. Shih et al., *Int. J. Cancer* 56:538 (1994). Immunostaining and in vivo radioimmunodetection studies have demonstrated the excellent sensitivity of LL2 in detecting B-cell lymphomas. Pawlak-Byczkowska et al., *Cancer Res.* 49:4568 (1989); Murthy et al., *Eur. J. Nucl. Med.* 19:394 (1992). Moreover, $^{99m}$Tc-labeled LL2-Fab' fragments have been shown to be useful in following upstaging of B-cell lymphomas, white $^{131}$I-labeled intact LL2 and labeled LL2 $F(ab')_2$ fragments have been used to target lymphoma sites and to induce therapeutic responses. Murthy et al., *Eur. J. Nucl. Med.* 19:394 (1992); Mills et al., *Proc. Am. Assoc. Cancer Res.* 34:479 (1993) [Abstract 2857]; Baum et al., *Cancer* 73 (*Suppl.* 3):896 (1994); Goldenberg et al., *J. Clin. Oncol.* 9:548 (1991). Furthermore, Fab' LL2 fragments conjugated with a derivative of *Pseudomonas* exotoxin has been shown to induce complete remissions for measurable human lymphoma xenografts growing in nude mice. Kreitman et al., *Cancer Res.* 53:819 (1993).

In an additional embodiment, an antibody of the present invention is a chimeric antibody in which the variable regions of a human antibody have been replaced by the variable regions of a rodent anti-CD22 or anti-CD19 antibody. The advantages of chimeric antibodies include decreased immunogenicity and increased in vivo stability.

Techniques for constructing chimeric antibodies are well-known to those of skill in the art. As an example, Leung et al., *Hybridoma* 13:469 (1994), describe how they produced an LL2 chimera by combining DNA sequences encoding the $V_\kappa$ and $V_H$ domains of LL2 monoclonal antibody with respective human κ and $IgG_1$ constant region domains. This publication also provides the nucleotide sequences of the LL2 light and heavy chain variable regions, $V_\kappa$ and $V_H$, respectively.

In another embodiment, an antibody of the present invention is a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46: 310 (1990).

In yet another embodiment, an antibody of the present invention is a "humanized" monoclonal antibody. That is, mouse complementarity determining regions are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of Orlandi et al., *Proc. Nat'l Acad. Sci. USA* 86: 3833 (1989). Techniques for producing humanised monoclonal antibodies are described, for example, by Jones et al., *Nature* 321:522 (1986), Riechmann et al., *Nature* 332:323 (1988), Verhoeyen et al., *Science* 239: 1534 (1988), Carter et al., *Proc. Nat'l Acad. Sci. USA* 89:4285 (1992), Sandhu, *Crit. Rev. Biotech.* 12:437 (1992), and Singer et al., *J. Immun.* 150:2844 (1993). The publication of Leung et al., *Mol. Immunol.* 32:1413 (1995), describes the construction of humanized LL2 antibody.

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994).

4. Production of Antibody Fragments

The present invention contemplates the use of fragments of anti-CD22 and anti-CD19 antibodies or other therapeutically useful antibodies. Antibody fragments can be prepared by proteolytic hydrolysis of an antibody or by expression in *E. coli* of the DNA coding for the fragment.

Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein. Also, see Nisonoff et al., *Arch Biochem. Biophys.* 89:230 (1960); Porter, *Biochem. J.* 73:119 (1959), Edelman et al., in METHODS IN ENZYMOLOGY VOL. 1, page 422 (Academic Press 1967), and Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, for example, Sandhu, supra.

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2:97 (1991). Also see Bird et al., *Science* 242:423 (1988), Ladner et al., U.S. Pat. No. 4,946,778, Pack et al., *Bio/Technology* 11:1271 (1993), and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

5. Preparation of Immunoconjugates

The present invention contemplates the use of "naked" anti-CD22 and anti-CD19 antibodies, as well as the use of immunoconjugates to effect treatment of B-cell malignancies. Such immunoconjugates can be prepared by indirectly conjugating a therapeutic agent to an antibody component. General techniques are described in Shih et al., *Int. J. Cancer* 41:832-839 (1988); Shih et al., *Int. J. Cancer* 46:1101-1106 (1990); and Shih et al., U.S. Pat. No. 5,057,313. The general method involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer is preferably an aminodextran or polypeptide of at least 50 amino acid residues, although other substantially equivalent polymer carriers can, also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate. In particular, an aminodextran will be preferred.

The process for preparing an immunoconjugate with an aminodextran carrier typically begins with a dextran polymer, advantageously a dextran of average molecular weight of about 10,000-100,000. The dextran is reacted with an oxidizing agent to effect a controlled oxidation of a portion of its carbohydrate rings to generate aldehyde groups. The oxidation is conveniently effected with glycolytic chemical reagents such as $NaIO_4$, according to conventional procedures.

The oxidized dextran is then reacted with a polyamine, preferably a diamine and more preferably, a mono- or polyhydroxy diamine. Suitable amines include ethylene diamine, propylene diamine, or other like polymethylene diamines, diethylene triamine or like polyamines, 1.3-diamino-2-hydroxypropane, or other like hydroxylated diamines or polyamines, and the like. An excess of the amine relative to the aldehyde groups of the dextran is used to insure substantially complete conversion of the aldehyde functions to Schiff base groups.

A reducing agent, such as $NaBH_4$, $NaBH_3CN$ or the like, is used to effect reductive stabilization of the resultant Schiff base intermediate. The resultant adduct can be purified by passage through a conventional sizing column to remove cross-linked dextrans.

Other conventional methods of derivatizing a dextran to introduce amine functions can also be used, e.g., reaction with cyanogen bromide, followed by reaction with a diamine.

The aminodextran is then reacted with a derivative of the particular drug, toxin, chelator, immnomodulator, boron addend, or other therapeutic agent to be loaded, in an activated form, preferably, a carboxyl-activated derivative, prepared by conventional means, e.g., using dicyclohexylcarbodiimide (DCC) or a water soluble variant thereof, to form an intermediate adduct.

Alternatively, polypeptide toxins such as pokeweed antiviral protein or ricin A-chain, and the like, can be coupled to aminodextran by glutaraldehyde condensation or by reaction of activated carboxyl groups on the protein with amines on the aminodextran.

Chelators for radiometals or magnetic resonance enhancers are well-known in the art. Typical are derivatives of ethylenediaminetetraacetic acid (EDTA) and diethylenetriaminepentaacetic acid (DTPA). These chelators typically have groups on the side chain by which the chelator can be attached to a carrier. Such groups include, e.g., benzylisothiocyanate, by which the DTPA or EDTA can be coupled to the amine group of a carrier. Alternatively, carboxyl groups or amine groups on a chelator can be coupled to a carrier by activation or prior derivatization and then coupling, all by well-known means.

Boron addends, such as carboranes, can be attached to antibody components by conventional methods. For example, carboranes can be prepared with carboxyl functions on pendant side chains, as is well known in the art. Attachment of such carboranes to a carrier, e.g., aminodextran, can be achieved by activation of the carboxyl groups of the carboranes and condensation with amines on the carrier to produce an intermediate conjugate. Such intermediate conjugates are then attached to antibody components to produce therapeutically useful immunoconjugates, as described below.

A polypeptide carrier can be used instead of aminodextran, but the polypeptide carrier must have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, copolymers thereof, and mixed polymers of these amino acids and others, e.g., serines, to confer desirable solubility properties on the resultant loaded carrier and immunoconjugate.

Conjugation of the intermediate conjugate with the antibody component is effected by oxidizing the carbohydrate portion of the antibody component and reacting the resulting aldehyde (and ketone) carbonyls with amine groups remaining on the carrier after loading with a drug, toxin, chelator, immunomodulator, boron addend, or other therapeutic agent. Alternatively, an intermediate conjugate can be attached to an oxidized antibody component via amine groups that have been introduced in the intermediate conjugate after loading with the therapeutic agent. Oxidation is conveniently effected either chemically, e.g., with $NaIO_4$ or other glycolytic reagent, or enzymatically, e.g., with neuraminidase and galactose oxidase. In the case of an aminodextran carrier, not all of the amines of the aminodextran are typically used for loading a therapeutic agent. The remaining amines of aminodextran condense with the oxidized antibody component to form Schiff base adducts, which are then reductively stabilized, normally with a borohydride reducing agent.

Analogous procedures are used to produce other immunoconjugates according to the invention. Loaded polypeptide carriers preferably have free lysine residues remaining for condensation with the oxidized carbohydrate portion of an antibody component. Carboxyls on the polypeptide carrier can, if necessary, be converted to amines by, e.g., activation with DCC and reaction with an excess of a diamine.

The final immunoconjugate is purified using conventional techniques, such as sizing chromatography on Sephacryl S-300.

Alternatively, immunoconjugates can be prepared by directly conjugating an antibody component with a therapeutic agent. The general procedure is analogous to the indirect method of conjugation except that a therapeutic agent is directly attached to an oxidized antibody component.

It will be appreciated that other therapeutic agents can be substituted for the chelators described herein. Those of skill in the art will be able to devise conjugation schemes without undue experimentation.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

As described above, carbohydrate moieties in the Fc region of an antibody can be used to conjugate a therapeutic agent. However, the Fc region is absent if an antibody fragment is used as the antibody component of the immunoconjugate. Nevertheless, it is possible to introduce a carbohydrate moiety into the light chain variable region of an antibody or antibody fragment. See, for example, Leung et al., J. Immunol. 154:5919 (1995): Hansen et al., U.S. Pat. No. 5,443,953 (1995). The engineered carbohydrate moiety is then used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a "divalent immunoconjugate" by attaching therapeutic agents to a carbohydrate moiety and to a free sulfhydryl group. Such a free sulfhydryl group may be located in the hinge region of the antibody component.

6. Preparation of Fusion Proteins

The present invention contemplates the use of fusion proteins comprising one or more antibody moieties and an immunomodulator or toxin moiety. Useful antibody moieties include antibody components that bind with CD19, CD20, CD22, CD52 or CD74, and a fusion protein may comprise one, two, three, four or all five of these antibody types. Bivalent, trivalent, tetravalent and quintavalent constructs can be used in accordance with the invention.

Methods of making antibody-immunomodulator fusion proteins are known to those of skill in the art. For example, antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., Hum. Antibodies Hybridomas 6:129 (1995), describe a fusion protein that includes an F(ab')$_2$ fragment and a tumor necrosis factor alpha moiety. Moreover, the therapeutic use of an hLL2-IL-2 fusion protein is illustrated by Example 5 of the present application.

Methods of making antibody-toxin fusion proteins in which a recombinant molecule comprises one or more antibody components and a toxin or chemotherapeutic agent also are known to those of skill in the art. For example, antibody-Pseudomonas exotoxin A fusion proteins have been described by Chaudhary et al., Nature 339:394 (1989), Brinkman et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., 2-6 Apr., 1995, Part 1, BIOT005. As a further example, Dohlsten et al., *Proc. Nat'l Acad. Sci. USA* 91:8945 (1994), reported an antibody-toxin fusion protein comprising *Staphylococcal* enterotoxin-A.

Illustrative of toxins which are suitably employed in the preparation of such conjugates are ricin, abrin, ribonuclease, DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., *Cell* 47:641 (1986), and Goldenberg, *CA—A Cancer Journal for Clinicians* 44:43 (1994). Other suitable toxins are known to those of skill in the art.

7. Coupling of Antibodies, Immunoconjugates and Fusion Proteins to Lipid Emulsions Long-circulating sub-micron lipid emulsions, stabilized with poly(ethylene glycol)-modified phosphatidylethanolamine (PEG-PE), can be used as drug carriers for the anti-CD22 and anti-CD19 antibody components, immunoconjugates, and fusion proteins of the present invention. The emulsions are composed of two major parts: an oil core, e.g., triglyceride, stabilized by emulsifiers, e.g., phospholipids. The poor emulsifying properties of phospholipids can be enhanced by adding a biocompatible co-emulsifier such as polysorbate 80. In a preferred embodiment, the anti-CD22 and anti-CD19 antibody components, immunoconjugates and fusion proteins are conjugated to the surface of the lipid emulsion globules with a poly(ethylene glycol)-based, heterobifunctional coupling agent, poly(ethylene glycol)-vinylsulfone-N-hydroxy-succinimidyl ester (NHS-PEG-VS).

The submicron lipid emulsion is prepared and characterized as described. Lundberg, *J. Pharm. Sci.*, 83:72 (1993); Lundberg et al., *Int. J. Pharm.*, 134:119 (1996). The basic composition of the lipid emulsion is triolein:DPPC:polysorbate 80, 2:1:0.4 (w/w). When indicated, PEG-DPPE is added into the lipid mixture at an amount of 2-8 mol % calculated on DPPC.

The coupling procedure starts with the reaction of the NHS ester group of NHS-PEG-VS with the amino group of distearoyl phosphatidyl-ethanolamine (DSPE). Twenty-five µmol of NHS-PEG-VS are reacted with 23 µmol of DSPE and 50 µmol triethylamine in 1 ml of chloroform for 6 hours at 40° C. to produce a poly(ethylene glycol) derivative of phosphatidyl-ethanolamine with a vinylsulfone group at the distal terminus of the poly(ethylene glycol) chain (DSPE-PEG-VS). For antibody conjugation. DSPE-PEG-VS is included in the lipid emulsion at 2 mol % of DPPC. The components are dispersed into vials from stock solutions at −20° C., the solvent is evaporated to dryness under reduced pressure. Phosphate-buffered saline (PBS) is added, the mixture is heated to 50° C., vortexed for 30 seconds and sonicated with a MSE probe sonicator for 1 minute. Emulsions can be stored at 4° C., and preferably are used for conjugation within 24 hours.

Coupling of anti-CD22 or anti-CD19 antibodies to emulsion globules is performed via a reaction between the vinylsulfone group at the distal PEG terminus on the surface of the globules and free thiol groups on the antibody. Vinylsulfone is an attractive derivative for selective coupling to thiol groups. At approximately neutral pH, VS will couple with a half life of 15-20 minutes to proteins containing thiol groups. The reactivity of VS is slightly less than that of maleimide, but the VS group is more stable in water and a stable linkage is produced from reaction with thiol groups.

Before conjugation, the antibody is reduced by 50 nM 2-mercaptoethanol for 10 minutes at 4° C. in 0.2 M Tris buffer (pH 8.7). The reduced antibody is separated from excess 2-mercaptoethanol with a Sephadex G-25 spin column, equilibrated in 50 nM sodium acetate buffered 0.9% saline (pH 5.3). The product is assayed for protein concentration by measuring its absorbance at 280 nm (and assuming that a 1 mg/ml antibody solution of 1.4) or by quantitation of $^{125}$I-labeled antibody. Thiol groups are determined with ALDRITHIOL™ (2,2'-dipyridyl disulfide) following the change in absorbance at 343 nm and with cystein as standard.

The coupling reaction is performed in HEPES-buffered saline (pH 7.4) overnight at ambient temperature under argon. Excess vinylsulfone groups are quenched with 2 mM 2-mercaptoethanol for 30 minutes, excess 2-mercaptoethanol and antibody are removed by gel chromatography on a Sepharose CL-4B column. The immunoconjugates are collected near the void volume of the column, sterilized by passage through a 0.45 µm sterile filter, and stored at 4° C.

Coupling efficiency is calculated using $^{125}$I-labeled antibody. Recovery of emulsions is estimated from measurements of [$^{14}$C]DPPC in parallel experiments. The conjugation of reduced LL2 to the VS group of surface-grafted DSPE-PEG-VS is very reproducible with a typical efficiency of near 85%.

8. Therapeutic Use of Anti-CD22 and Anti-CD19 Antibodies in Simple and Multimodal Regimens The present invention contemplates the use of naked anti-CD22 and anti-CD19 antibodies, or immunoconjugates or fusion proteins comprising anti-CD22 or anti-CD19 antibodies, as the primary therapeutic composition for treatment of B-cell malignancies. Such a composition can contain polyclonal anti-CD22 or anti-CD19 antibodies or monoclonal anti-CD22 or anti-CD19 antibodies.

In addition, a therapeutic composition of the present invention can contain a mixture of monoclonal anti-CD22 antibodies directed to different, non-blocking CD22 epitopes, or a mixture of monoclonal anti-CD19 antibodies directed to different, non-blocking CD19 epitopes. Monoclonal antibody cross-inhibition studies have identified five epitopes on CD22, designated as epitopes A-E. See, for example, Schwartz-Albiez et al., "The Carbohydrate Moiety of the CD22 Antigen Can Be Modulated by Inhibitors of the Glycosylation Pathway," in LEUKOCYTE TYPING IV. WHITE CELL DIFFERENTIATION ANTIGENS, Knapp et al. (eds.), p. 65 (Oxford University Press 1989). As an illustration, the LL2 antibody binds with epitope B. Stein et al., *Cancer Immunol. Immunother.* 37:293 (1993). Accordingly, the present invention contemplates therapeutic compositions comprising a mixture of monoclonal anti-CD22 antibodies that bind at least two CD22 epitopes. For example, such a mixture can contain monoclonal antibodies that bind with at least two CD22 epitopes selected from the group consisting of epitope A, epitope B, epitope C, epitope D and epitope E. Similarly, the present invention contemplates therapeutic compositions comprising a mixture of monoclonal anti-CD19 antibodies that bind at least two CD19 epitopes.

Methods for determining the binding specificity of an anti-CD22 antibody are well-known to those of skill in the art. General methods are provided, for example, by Mole, "Epitope Mapping," in METHODS IN MOLECULAR BIOLOGY, VOLUME 10: IMMUNOCHEMICAL PROTOCOLS, Manson (ed.), pages 105-116 (The Humana Press, Inc. 1992). More specifically, competitive blocking assays to determine CD22 epitope specificity are described by Stein et al., *Cancer Immunol. Immunother.* 37:293 (1993), and by Tedder et al., U.S. Pat. No. 5,484,892 (1996).

The Tedder patent also describes the production of CD22 mutants which lack one or more immunoglobulin-like domains. These mutant proteins were used to determine that immunoglobulin-like domains 1, 2, 3, and 4 correspond with epitopes A, D, B, and C, respectively. Thus, CD22 epitope specificity can also be identified by binding a test antibody with a panel of CD22 proteins lacking particular immunoglobulin-like domain.

Although naked anti-CD22 antibodies or anti-CD19 antibodies are the primary therapeutic compositions for treatment of B-cell malignancies, the efficacy of such antibody therapy can be enhanced by supplementing naked antibodies with immunoconjugates, fusion proteins, and other forms of supplemental therapy described herein. In such multimodal regimens, the supplemental therapeutic compositions can be administered before, concurrently or after administration of the naked anti-CD22 or anti-CD19 antibodies.

The therapeutic compositions described herein are particularly useful for treatment of indolent forms of B-cell lymphomas, aggressive forms of B-cell lymphomas, chronic lymphatic leukemias, and acute lymphatic leukemias. For example, anti-CD22 antibody components and immunoconjugates can be used to treat both indolent and aggressive forms of non-Hodgkin's lymphoma.

A radiolabeled antibody, immunoconjugate or fusion protein may comprise an α-emitting radioisotope, a β-emitting radioisotope, a γ-emitting radioisotope, an Auger electron emitter, a neutron capturing agent that emits α-particles or a radioisotope that decays by electron capture. Suitable radioisotopes include $^{198}Au$, $^{32}P$, $^{125}I$, $^{131}I$, $^{90}Y$, $^{186}Re$, $^{188}Re$, $^{67}Cu$, $^{211}At$, $^{213}Bi$, $^{224}Ac$, and the like.

As discussed above, a radioisotope can be attached to an antibody component directly or indirectly, via a chelating agent. For example, $^{67}Cu$, considered one of the more promising radioisotopes for radioimmunotherapy due to its 61.5 hour half-life and abundant supply of beta particles and gamma rays, can be conjugated to an antibody component using the chelating agent, p-bromoacetamido-benzyl-tetraethylaminetetraacetic acid (TETA). Chase, "Medical Applications of Radioisotopes," in REMINGTON'S PHARMACEUTICAL SCIENCES, 18th Edition, Gennaro et al. (eds.), pages 624-652 (Mack Publishing Co. 1990). Alternatively, $^{90}Y$, which emits an energetic beta particle, can be coupled to an antibody component using diethylenetriaminepentaacetic acid (DTPA). Moreover, a method for the direct radiolabeling of the antibody component with $^{131}I$ is described by Stein et al., Antibody Immunoconj. Radiopharm. 4: 703 (1991).

Alternatively, boron addends such as carboranes can be attached to antibody components, as discussed above.

Preferred immunoconjugates and fusion proteins include antibody components and conjugates of an anti-CD22 or anti-CD19 antibody component and an immunomodulator. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10 and IL-12), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, interferon-γ, TNF-α, and the like. Alternatively, subjects can receive naked anti-CD22 or naked anti-CD19 antibodies and a separately administered cytokine, which can be administered before, concurrently or after administration of the naked anti-CD22 or anti-CD19 antibodies. The cytokines enhance the activity of ADCC/NK, the effector cells that effect kill of tumor cells by binding to the Fc domain of human IgG1 antibodies, a domain that is present in hLL2.

Antibody-immunomodulator immunoconjugates and antibody-immunomodulator fusion proteins provide a means to deliver an immunomodulator to a target cell and are particularly useful against tumor cells. The cytotoxic effects of immunomodulators are well known to those of skill in the art. See, for example, Klegerman et al., "Lymphokines and Monokines," in BIOTECHNOLOGY AND PHARMACY, Pessuto et al. (eds.), pages 53-70 (Chapman & Hall 1993). As an illustration, interferons can inhibit cell proliferation by inducing increased expression of class I histocompatibility antigens on the surface of various cells and thus, enhance the rate of destruction of cells by cytotoxic T lymphocytes. Furthermore, tumor necrosis factors, such as TNF-α, are believed to produce cytotoxic effects by inducing DNA fragmentation.

Useful cancer chemotherapeutic drugs for the preparation of immunoconjugates and fusion proteins include nitrogen mustards, alkyl sulfonates, nitrosoureas, triazenes, folic acid analogs, pyrimidine analogs, purine analogs, antibiotics, epipodophyllotoxins, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985). Other suitable chemotherapeutic agents, such as experimental drugs, are known to those of skill in the art.

In addition, therapeutically useful immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130:1473 (1983); idem., Cancer Res. 45:4380 (1985); Oseroff et al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes. Multimodal therapies of the present invention further include immunotherapy with naked anti-CD22 and naked anti-CD19 antibodies supplemented with administration of anti-CD19 and anti-CD22 antibodies, respectively, as well as with the co-administration of anti-CD20, CD52 and/or CD74 antibodies in the form of naked antibodies or as immunoconjugates. Anti-CD19 and anti-CD20 antibodies are known to those of skill in the art. See, for example, Ghetie et al., Cancer Res. 48:2610 (1988): Hekman et al., Cancer Immunol. Immunother. 32:364 (1991); Kaminski et al., N. Engl. J. Med. 329:459 (1993): Press et al., N. Engl. J. Med. 329:1219 (1993); Maloney et al., Blood 84:2457 (1994); Press et al., Lancet 346:336 (1995); Longo, Curr. Opin. Oncol. 8:353 (1996).

In another form of multimodal therapy, subjects receive naked anti-CD22 or naked anti-CD19 antibodies, and/or immunoconjugates or fusion proteins, in conjunction with standard cancer chemotherapy. For example, "CVB" (1.5 g/m² cyclophosphamide, 200-400 mg/m² etoposide, and 150-200 mg/m² carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a preferred multimodal therapy, both chemotherapeutic drugs and cytokines are co-administered with an antibody, immunoconjugate or fusion protein according to the present invention. The cytokines, chemotherapeutic drugs and antibody, immunoconjugate or fusion protein can be administered in any order, or together.

In general, the dosage of administered anti-CD22 and anti-CD19 antibodies, anti-CD22 and anti-CD19 antibody components. immunoconjugates, and fusion proteins will vary depending upon such factors as the patient's age, weight, height, sex, general medical condition and previous medical history. Typically, it is desirable to provide the recipient with a dosage of antibody component, immunoconjugate or fusion protein which is in the range of from about 1 pg/kg to 10 mg/kg (amount of agent/body weight of patient), although a lower or higher dosage also may be administered as circumstances dictate.

Administration of antibody components, immunoconjugates or fusion proteins to a patient can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Those of skill in the art are aware that intravenous injection provides a useful mode of administration due to the thoroughness of the circulation in rapidly distributing antibodies. Intravenous administration, however, is subject to limitation by a vascular barrier comprising endothelial cells of the vasculature and the subendothelial matrix. Still, the vascular barrier is a more notable problem for the uptake of therapeutic antibodies by solid tumors. Lymphomas have relatively high blood flow rates, contributing to effective antibody delivery. Intralymphatic routes of administration, such as subcutaneous or intramuscular injection, or by catheterization of lymphatic vessels, also provide a useful means of treating lymphomas.

Preferably, naked anti-CD22 or anti-CD19 antibodies are administered at low protein doses, such as 20 to 1500 milligrams protein per dose, given once, or repeatedly, parenterally. Alternatively, naked anti-CD22 or anti-CD19 antibodies are administered in doses of 20 to 1000 milligrams protein per dose, or 20 to 500 milligrams protein per dose, or 20 to 100 milligrams protein per dose.

As described above, the present invention also contemplates therapeutic methods in which naked anti-CD22 or anti-CD 19 antibody components are supplemented with immunoconjugate or fusion protein administration. In one variation, naked anti-CD22 or anti-CD19 antibodies are administered with low-dose radiolabeled anti-CD22 or anti-CD19 antibodies or fragments. As a second alternative, naked anti-CD22 or anti-CD19 antibodies are administered with low-dose radiolabeled anti-CD22-cytokine or anti-CD19-cytokine immunoconjugates. As a third alternative, naked anti-CD22 or anti-CD19 antibodies are administered with anti-CD22-cytokine or anti-CD19-cytokine immunoconjugates that are not radiolabeled. With regard to "low doses" of $^{131}$I-labeled immunoconjugates, a preferable dosage is in the range of 15 to 40 mCi, while the most preferable range is 20 to 30 mCi. In contrast, a preferred dosage of $^{90}$Y-labeled immunoconjugates is in the range from 10 to 30 mCi, while the most preferable range is 10 to 20 mCi. Preferred antibody components include antibodies and fragments derived from LL2 antibodies, including murine LL2 monoclonal antibody, chimeric LL2 antibody, and humanized LL2 antibody.

Immunoconjugates having a boron addend-loaded carrier for thermal neutron activation therapy will normally be effected in similar ways. However, it will be advantageous to wait until non-targeted immunoconjugate clears before neutron irradiation is performed. Clearance can be accelerated using an antibody that binds to the immunoconjugate. See U.S. Pat. No. 4,624,846 for a description of this general principle.

The anti-CD22 and anti-CD19 antibody components, immunoconjugates and fusion proteins alone, or conjugated to liposomes, can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (1995).

For purposes of therapy, antibody components (or immunoconjugates/fusion proteins) and a pharmaceutically acceptable carrier are administered to a patient in a therapeutically effective amount. A combination of an antibody component, optionally with an immunoconjugate/fusion protein, and a pharmaceutically acceptable carrier is said to be administered in a "therapeutically effective amount" if the amount administered is physiologically significant. An agent is pnysiologically significant if its presence results in a detectable change in the physiology of a recipient patient. In the present context, an agent is physiologically significant if its presence results in the inhibition of the growth of target tumor cells.

Additional pharmaceutical methods may be employed to control the duration of action of an antibody component, immunoconjugate or fusion protein in a therapeutic application. Control release preparations can be prepared through the use of polymers to complex or adsorb the antibody component, immunoconjugate or fusion protein. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446 (1992). The rate of release of an antibody component (or immunoconjugate) from such a matrix depends upon the molecular weight of the protein, the amount of antibody component/immunoconjugate/fusion protein within the matrix, and the size of dispersed particles. Saltzman et al., *Biophys. J.* 55:163 (1989); Sherwood et al., supra.

Other solid dosage forms are described in REMINGTON'S PHARMACEUTICAL SCIENCES, 19th ed. (1995).

The present invention also contemplates a method of treatment in which immunomodulators are administered to prevent, mitigate or reverse radiation-induced or drug-induced toxicity of normal cells, and especially hematopoietic cells. Adjunct immunomodulator therapy allows the administration of higher doses of cytotoxic agents due to increased tolerance of the recipient mammal. Moreover, adjunct immunomodulator therapy can prevent, palliate, or reverse dose-limiting marrow toxicity. Examples of suitable immunomodulators for adjunct therapy include G-CSF, GM-CSF, thrombopoietin, IL-1, IL-3, IL-12, and the like. The method of adjunct immunomodulator therapy is disclosed by Goldenberg, U.S. Pat. No. 5,120,525.

For example, recombinant IL-2 may be administered intravenously as a bolus at $6 \times 10^5$ IU/kg or as a continuous infusion at a dose of $18 \times 10^6$ IU/m²/d. Weiss et al., *J. Clin. Oncol.* 10:275 (1992). Alternatively, recombinant IL-2 may be administered subcutaneously at a dose of $12 \times 10^6$ IU. Vogelzang et al., *J. Clin. Oncol.* 11:1809 (1993). Moreover, INF-γ may be administered subcutaneously at a dose of $1.5 \times 10^6$ U. Lienard et al., *J. Clin. Oncol.* 10:52 (1992). Furthermore, Nadeau et al., *J. Pharmacol. Exp. Ther.* 274:78 (1995), have shown that a single intravenous dose of recombinant IL-12 (42.5 μg/kilogram) elevated IFN-γ levels in rhesus monkeys.

Suitable IL-2 formulations include PROLEUKIN® (IL-2 aldesleukin) (Chiron Corp./Cetus Oncology Corp.; Emeryville, Calif.) and TECELEUKIN® (Interleukin-2) (Hoffmann-La Roche, Inc.; Nutley, N.J.). ACTIMMUNE® (Interferon gamma-1b) (Genentech Inc.; South San Francisco, Calif.) is a suitable INF-γ preparation.

The present invention, thus generally described, will be understood more readily by reference to the following examples, which are provided by way of illustration and are not intended to be limiting of the present invention.

EXAMPLE 1

Treatment of a Patient with Indolent Lymphoma in Lymph Nodes and Bone Marrow

A patient presents with diffuse large cell aggressive lymphoma. The patient was placed on COP with minimal response. Seven months later, the patient underwent CDA therapy with good response. However, fifteen months later, the patient was characterized as having progressive lymphadenopathy, and seven months after this was found to have extensive lymphoma infiltration of bone marrow, extensive lymphoadenopathy of neck, chest, abdomen, pelvis, and hepatosplenomegaly (Day 0).

The patient then began therapy with humanized LL2 monoclonal antibody. The patient was infused intravenously with 634 mg of humanized LL2 antibody, and the treatment was repeated 6, 13, and 20 days following this initial treatment. Immediately following the last dose, the serum value of hLL2 was 389.7 μg/ml, and one month following the last dose the serum value of hLL2 was 186.5 μg/ml.

Five months after the final dose of hLL2, a computerized tomography scan of the patient showed no evidence of lymphoma, resolution of splenomegaly, and no liver abnormality, and subsequent histology with immunoperoxidase staining of paraffin tissue sections for CD20 and CD3 reveals no evidence of lymphoma in bone marrow. Normal B-cells in the blood prior to therapy with hLL2 were completely depleted from the blood 2 months post-therapy, and there was minimal reappearance of normal B cells five months post-therapy. The results are shown in the following tables.

TABLE 1

B-cells and T-cells in marrow

| Day | % marrow B-cells | | | | % marrow T-cells | % marrow HLA-Dr |
|-----|------|------|-------|--------|------|------|
| | CD19 | CD20 | Kappa | lambda | CD3 | (Ia) |
| Flow cytometry | | | | | | |
| 0 | 12 | 15 | 20 | 3 | 7 | 20 |
| Conventional histology | | | | | | |
| 0 | 30 and 40% malignant lymphoma cells in two aspirates | | | | | |
| 28 | hLL2 therapy | | | | | |
| 34 | hLL2 therapy | | | | | |
| 41 | hLL2 therapy | | | | | |
| 48 | hLL2 therapy | | | | | |
| Flow cytometry | | | | | | |
| 203 | 3 | 1 | 1 | <1 | 32 | 2 |
| Immunoperoxidase staining of paraffin tissue sections for CD20 and CD3 | | | | | | |
| 203 | 5 | | | | 95 | |
| Conventional histology | | | | | | |
| 203 | Small lymphoid aggregates/hypocellularity with myeloid hypoplasia | | | | | |

TABLE 2

B-cells and T-cells in blood

| Day | T4/T8 | % blood B-cells | | | | % blood T-cells | % blood HLA-Dr |
|-----|-------|------|------|-------|--------|------|------|
| | | CD19 | CD20 | kappa | lambda | CD3 | (Ia) |
| Flow cytometry | | | | | | | |
| 0 | 1.5 | 5 | 5 | 6 | 2 | 38 | 6 |
| 28 | | hLL2 therapy | | | | | |
| 34 | | hLL2 therapy | | | | | |
| 41 | | hLL2 therapy | | | | | |
| 48 | | hLL2 therapy | | | | | |
| Flow cytometry | | | | | | | |
| 76 | 1.3 | <1 | <1 | <1 | <1 | 71 | 6 |
| 191 | 2.0 | 1 | 1 | <1 | <1 | 73 | 4 |

EXAMPLE 2

Treatment of a Patient With Aggressive. Diffuse. Large Cell Lymphoma in Lung and Liver A patient presents with diffuse, large cell, malignant lymphoma, in lung and liver. The patient has a good, but short, response to CHOP. Seven months later, the patient receives high dose chemotherapy along with a bone marrow transplant. Ten months later, the patient relapses, with lung, liver and lymphoadenopathy, and is treated with four standard doses of Rituxan. The patient had a brief response to the Rituxan, which lasted less than 3 months. The patient then failed a second treatment with Rituxan, and was characterized as having progressive lymphoma with lung, liver and lymphoadenopathy (Day 0).

The patient then began therapy with humanized LL2 monoclonal antibody. The patient was infused intravenously with 556 mg of humanized LL2 antibody, and the treatment was repeated 5, 12, and 19 days following this initial treatment. Immediately following the last dose, the serum value of hLL2 was 279.8 μg/ml, and one month following the last dose the serum value of hLL2 was 99.1 μg/ml.

Prior to treatment, a CT scan of the patient showed three lung lesions, 3.96, 4,83 and 4.6 cm², respectively. One month after the final dose of hLL2, a CT scan of the patient showed the lesions were reduced to 0, 1.21 and 0.81 cm², respectively. Four and a half months after the final dose of hLL2, a CT scan showed the three lesions were reduced to 0, 1 and 0 cm², respectively.

Normal B-cells in the blood prior to therapy were markedly reduced, probably due to the Rituxan therapy. There was minimal reappearance of normal B cells one month post-therapy. The results are shown in the following tables.

TABLE 3

B-cells and T-cells in marrow

| Day | % marrow B-cells | | | | % marrow T-cells | % marrow HLA-Dr |
|---|---|---|---|---|---|---|
|  | CD19 | CD20 | kappa | lambda | CD3 | (Ia) |
| | | | Flow cytometry | | | |
| 0 | 80 | | | | 20 | |
| | Conventional histology | | | | | |
| 28 | negative for lymphoma | | | | | |
| 28 | hLL2 therapy | | | | | |
| 33 | hLL2 therapy | | | | | |
| 40 | hLL2 therapy | | | | | |
| 47 | hLL2 therapy | | | | | |

TABLE 4

B-cells and T-cells in blood

| Day | T4/T8 | % blood B-cells | | | | % blood T-cells | % blood HLA-Dr |
|---|---|---|---|---|---|---|---|
| | | CD19 | CD20 | kappa | lambda | CD3 | (Ia) |
| | | | | Flow cytometry | | | |
| 0 | 0.5 | <1 | <1 | <1 | <1 | 57 | 4 |
| 28 | | hLL2 therapy | | | | | |
| 33 | | hLL2 therapy | | | | | |
| 40 | | hLL2 therapy | | | | | |
| 47 | | hLL2 therapy | | | | | |
| | | | | Flow cytometry | | | |
| 48 | 0.3 | <3 | 1 | <1 | <1 | 68 | 4 |
| 76 | 0.4 | <1 | <1 | 1 | 1 | 63 | 15 |

TABLE 5

Results of CT scans

| Lesion Location | Day 19 | Day 50 | Day 182 |
|---|---|---|---|
| | | lesion size in cm² | |
| Left axillary | 6.82 | 4.18 | resolved |
| Portacaval | 20.16 | 5.04 | resolved |
| Retrocaval | 5.72 | 3.24 | resolved |
| Paraaortic | 4.00 | 2.88 | resolved |

EXAMPLE 3

Treatment of a Patient with Relapsed
Intermediate-Grade Non-Hodgkin's Lymphoma

A patient with intermediate grade non-Hodgkin's lymphoma has failed prior aggressive chemotherapy, consisting of CHOP×6, which led to a complete remission for five months, another course of CHOP×6, resulting in progression, D-MOPP×2, resulting in stable disease for six months, and CVB with peripheral stem cell transplantation, which led to a partial remission for four months. The patient presents with recurrent lymphoma in the chest and in a neck lymph node, both measurable by computerized tomography and palpation, respectively.

The patient is infused with 50 mg of humanized LL2 monoclonal antibody on days 2, 5, 9, 12 of two successive weeks with no adverse effects noted. Three weeks later, palpation of the neck node enlargement shows a measurable decrease of about 60%, while a repeat computerized tomography scan of the chest shows a marked, 70% reduction in tumor. Follow-up measurements made at ten weeks post therapy shows no evidence of the disease in the neck or the chest. Since new disease is not detected elsewhere, the patient is considered to be in complete remission. Follow-up studies every 10-12 weeks confirms a complete remission for at least 16 months post therapy.

EXAMPLE 4

Treatment of a Patient with Diffuse Large
Cell Aggressive Lymphoma With CHOP and hLL2

A patient presents with diffuse large cell aggressive lymphoma, and is diagnosed to have a poor prognosis, having bulky disease in the abdomen, numerous other sites of extranodal disease, and elevated serum lactate dehydrogenase (LDH). The patient is placed on CHOP, and after three cycles of therapy, a partial response is observed with resolution of numerous sites of extranodal disease outside the abdomen. However, the bulky disease in the abdomen continues to increase in volume, and the serum LDH remains elevated.

Upon initiation of the third cycle of CHOP, the patient is infused with 50 mg of humanized LL2 monoclonal antibody on days 2, 5, 9 and 12. This therapeutic regimen of hLL2 is repeated concomitantly with four more cycles of CHOP. During therapy, the serum LDH level falls to within the normal range. One month after the third cycle of CHOP and hLL2, a computerized tomography scan of the bulky tumor in the abdomen shows over a 90% shrinkage of the mass. Follow-up studies every 10-12 weeks confirms a complete remission for over nine months post-therapy.

EXAMPLE 5

Treatment of a Patient with Relapsed, Aggressive Large
Cell Lymphoma With hLL2 and hLL2-IL2

A patient with diffuse large cell aggressive lymphoma responds to first line (CHOP) and second line (m-BACOD) chemotherapy, but fails third line chemotherapy (MACOP-B). After completion of third line chemotherapy, the patient has diffuse disease in the bone marrow, massive splenomegaly, and numerous sites of enlarged lymph nodes that could be palpitated. The patient is then infused with 50 mg of humanized LL2 on days 2, 5, 9 and 12. This regimen is repeated every other week for four weeks. The bone marrow disease progressively responds to the hLL2 treatment, and the size of the nodes also decreases. However, many nodes can still be palpitated, and little decrease is observed in spleen size. While therapy with hLL2 continues every two weeks, the patient also receives 10 mg of hLL2-IL2 fusion protein. After the first treatment, there is a profound decrease in the size of the spleen, and after the second treatment with hLL2/hLL2-IL2, the nodes are not palpable, and the spleen has decreased further in size. No progression of the disease is observed for over six months.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains All publications and patent applications are herein incorporated by reference to the same extent as if each individual publication or patent application were specifically and individually indicated to be incorporated by reference in its entirety.

The invention claimed is:

1. A therapeutic composition comprising a combination of antibodies, wherein one of the antibodies is an anti-CD22 antibody and the other antibody is an anti-CD20 antibody.

2. The therapeutic composition according to claim 1, wherein the antibodies are packaged for concurrent administration.

3. The therapeutic composition according to claim 1, wherein the antibodies are packaged for separate administration.

4. The therapeutic composition according to claim 1, wherein at least one of the antibodies is a naked antibody.

5. The therapeutic composition according to claim 1, wherein at least one of the antibodies is conjugated to a drug.

6. The therapeutic composition according to claim 5, wherein the immunoconjugate comprises a chemotherapeutic drug.

7. The therapeutic composition according to claim 6, wherein the chemotherapeutic drug is selected from the group consisting of cyclophosphamide, etoposide, vincristine, procarbazine, prednisone, carmustine, doxorubicin, methotrexate, bleomycin, dexamethasone, phenyl butyrate, bryostatin-1 and leucovorin.

8. The therapeutic composition according to claim 1, wherein at least one of the antibodies is conjugated to a radiolabel.

9. The therapeutic composition according to claim 8, wherein the radiolabel is selected from the group consisting of $^{198}$Au, $^{32}$P, $^{125}$I, $^{90}$Y, $^{186}$Re, $^{88}$Re, $^{67}$Cu, $^{211}$At, and $^{131}$I.

10. The therapeutic composition according to claim 1, wherein at least one of the antibodies is conjugated to an immunomodulator.

11. The therapeutic composition according to claim 10, wherein the immunomodulator is selected from the group consisting of IL-1, IL-2, IL-3, IL-6 and IL-10, IL-12, interferon-α, interferon-β, interferon-γ, granulocyte-colony stimulating factor, granulocyte macrophage-colony stimulating factor and lymphotoxins.

12. The therapeutic composition according to claim 1, wherein the anti-CD22 antibody is a human antibody.

13. The therapeutic composition according to claim 1, wherein the anti-CD22 antibody is a humanized antibody.

14. The therapeutic composition according to claim 1, wherein the anti-CD22 antibody is a chimeric antibody.

15. The therapeutic composition according to claim 1, wherein the anti-CD22 antibody is hLL2.

16. The therapeutic composition according to claim 8, wherein the anti-CD22 antibody is radiolabeled with $^{90}$Y.

17. The therapeutic composition according to claim 8, wherein the anti-CD22 antibody is radiolabeled with $^{67}$Cu.

18. The therapeutic composition according to claim 1, wherein the anti-CD20 antibody is a chimeric antibody.

19. The therapeutic composition according to claim 15, wherein the anti-CD20 antibody is a chimeric antibody.

20. The therapeutic composition according to claim 1, wherein the anti-CD20 antibody is naked and the anti-CD22 antibody is conjugated to a therapeutic agent.

21. The therapeutic composition according to claim 20, wherein the anti-CD22 antibody is conjugated to a drug.

* * * * *